(12) United States Patent
Dyballa et al.

(10) Patent No.: US 9,950,979 B2
(45) Date of Patent: Apr. 24, 2018

(54) METHOD FOR PRODUCING ASYMMETRICAL BIPHENOLS USING SELENIUM DIOXIDE

(71) Applicants: Katrin Marie Dyballa, Recklinghausen (DE); Robert Franke, Marl (DE); Dirk Fridag, Haltern am See (DE); Michael Mirion, Mainz (DE); Thomas Quell, Mainz (DE); Siegfried R. Waldvogel, Gau-Algesheim (DE)

(72) Inventors: Katrin Marie Dyballa, Recklinghausen (DE); Robert Franke, Marl (DE); Dirk Fridag, Haltern am See (DE); Michael Mirion, Mainz (DE); Thomas Quell, Mainz (DE); Siegfried R. Waldvogel, Gau-Algesheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/313,606

(22) PCT Filed: May 20, 2015

(86) PCT No.: PCT/EP2015/061097
§ 371 (c)(1),
(2) Date: Nov. 23, 2016

(87) PCT Pub. No.: WO2015/181018
PCT Pub. Date: Dec. 3, 2015

(65) Prior Publication Data
US 2017/0204031 A1 Jul. 20, 2017

(30) Foreign Application Priority Data

May 26, 2014 (DE) .......... 10 2014 209 967
May 26, 2014 (DE) .......... 10 2014 209 974
May 26, 2014 (DE) .......... 10 2014 209 976

(51) Int. Cl.
*C07C 41/30* (2006.01)
(52) U.S. Cl.
CPC .................... *C07C 41/30* (2013.01)
(58) Field of Classification Search
CPC .................................................. C07C 41/30
See application file for complete search history.

(56) References Cited

U.S. PATENT DOCUMENTS

2008/0177113 A1* 7/2008 Bartsch .......... C07C 37/11
568/723

FOREIGN PATENT DOCUMENTS

CN 101817713 A * 9/2010 .......... C07B 37/00
WO 2010/139687 A1 12/2010

OTHER PUBLICATIONS

Waitkins et al. ("Selenium Dioxide: Preparation, Properties, and use as Oxidizing Agent", Research Laboratories, Canadian Copper Refiners Limited, Montreal East, Quebec Canada, Feb. 1945, pp. 235-289).*
Kirste et al. ("Highly Selective Electrosynthesis of Biphenols on Graphite Electrodes in Fluorinated Media", Chemistry, European Journal, vol. 17, 2011, pp. 14164-14169).*
International Search Report, PCT/EP2015/061097, dated Jul. 29, 2015.
Written Opinion, PCT/EP2015/061097, dated Jul. 29, 2015.
Bernd Elsler, et al; "Metal- and Reagent-Free Highly Selective Anodic Cross-Coupling Reaction of Phenols"; Angewandte Chemiei International Edition, Mar. 18, 2014, pp. n/a-n/a, XP55203477, ISSN: 1433-7851.
Elsler et al., "Metal- and reagent-free highly selective anodic cross-coupling reaction of phenols." Angew Chem Int Ed Engl. May 12, 2014;53(20):5210-3.
Chen et al., "Modified BINOL ligands in asymmetric catalysis." Chemical reviews 103.8 (2003): 3155-3212.
Brunel, "Update 1 of: BINOL: a versatile chiral reagent." Chemical reviews 107.9 (2007): PR1-PR45.
Kobayashi et al., "Catalytic enantioselective formation of C—C bonds by addition to imines and hydrazones: a ten-year update." Chemical reviews 111.4 (2011): 2626-2704.
Sartori et al., "Selective synthesis of unsymmetrical hydroxylated and methoxylated biaryls." J. Org. Chem., 1993, 58 (25), pp. 7271-7273.
Gaster et al., "Significant Enhancement in the Efficiency and Selectivity of Iron-Catalyzed Oxidative Cross-Coupling of Phenols by Fluoroalcohols." Angewandte Chemie International Edition 54.14 (2015): 4198-4202.
Hovorka et al., "Highly selective oxidative cross-coupling of substituted 2-naphthols: A convenient approach to unsymmetrical 1,1'-binaphthalene-2,2'-diols." Tetrahedron letters. 1990; 31(3):413-6.
Hovorka et al., "The oxidative cross-coupling of substituted 2-naphthols, part I: The scope and limitations." Tetrahedron 48.43 (1992): 9503-9516.
Hovorka et al., "The oxidative cross-coupling of substituted 2-napthols, part II: Selectivity as a mechanistic probe 1,." Tetrahedron, 1992; 48(43):9517-9530.
Bolm, "Cross-Coupling Reactions." Org. Lett., 2012, 14 (12), pp. 2925-2928.

(Continued)

*Primary Examiner* — Rosalynd A Keys
(74) *Attorney, Agent, or Firm* — Michael Best & Friedrich LLP

(57) ABSTRACT

A process for preparing unsymmetric biphenols, comprising: a) adding a first substituted phenol to the reaction mixture; b) adding a second substituted phenol having different substitution than the first phenol to the reaction mixture; c) adding selenium dioxide to the reaction mixture; d) adding a solvent; and e) heating the reaction mixture such that the first substituted phenol and the second phenol having different substitution are converted to an unsymmetric biphenol.

12 Claims, No Drawings

(56) References Cited

OTHER PUBLICATIONS

Kirste et al., "Anodic Phenol-Arene Cross-Coupling Reaction on Boron-Doped Diamond Electrodes." Angewandte Chemie International Edition, 2010; 49: 971-975.

Kirste et al., "Efficient Anodic and Direct Phenol-Arene C,C Cross-Coupling: The Benign Role of Water or Methanol." J. Am. Chem. Soc., 2012, 134 (7), pp. 3571-3576.

* cited by examiner

METHOD FOR PRODUCING ASYMMETRICAL BIPHENOLS USING SELENIUM DIOXIDE

The present invention relates to a process for preparing unsymmetric biphenols by means of use of selenium dioxide.

The direct coupling of phenols to give the corresponding biphenol derivatives which are of great industrial interest continues to be a challenge since these reactions are often neither regio-nor chemoselective.

Biaryl refers to compounds in which two aryl groups are joined to one another via a single bond. The simplest biaryl is biphenyl.

A biphenol is a biaryl substituted by at least two OH groups which bears one OH group on each aryl radical, and these are also referred to as dihydroxybiaryls. The umbrella terms "aryls" and "phenols" should be understood in this connection to mean both unsubstituted and substituted compounds. Substitution here is on the benzene ring.

Scheme 1: unsubstituted biphenol

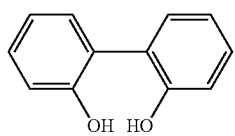

Biphenols serve as synthesis units for catalytically active substances and are therefore of industrial interest. These are employed particularly as ligand components for catalysts. In this case, the biphenol can be used, for example, as ligand unit in the enantioselective catalysis [cf. Y. Chen, S. Yekta, A. K. Yudin, Chem. Rev. 2003, 103, 3155-3211; J. M. Brunel Chem. Rev. 2005, 105, 857-898; S. Kobayashi, Y. Mori, J. S. Fossey, Chem. Rev. 2011, 11, 2626-2704].

The optimization of the substitution patterns of such skeletons determines the success of these transformations. However, ligands used to date very frequently have symmetric biphenol units. Ligand optimization in unsymmetric 2,2'- and 2,3'-biphenol systems has not been exhausted to date, because the direct synthesis thereof was hardly possible, or transition metal-catalyzed reactions would have been necessary.

Direct cross-coupling of unprotected phenol derivatives has been possible only in a few examples to date. For this purpose, usually superstoichiometric amounts of inorganic oxidizing agents such as $AlCl_3$, $FeCl_3$, or 2,3-dichloro-5,6-dicyano-1,4-benzoquinone (DDQ), which is organic, have been used [G. Sartori, R. Maggi, F. Bigi, M. Grandi, J. Org. Chem. 1993, 58, 7271]. Some examples with iron use peroxides as co-oxidant [E. Gaster, Y. Vainer, A. Regev, S. Narute, K. Sudheendran, A. Werbeloff, H. Shalit, D. Pappo, Angew. Chem. 2015 DOI:10.1002/ange.201409694].

It has likewise been possible to prepare a few unsymmetric binaphthol derivatives by oxidation of two naphthols with $CuCl_2$. [a) M. Hovorka, J. Günterova, J. Závada, Tetrahedron Lett. 1990, 31, 413; b) M. Hovorka, R. Ščigel, J. Gunterová, M. Tichý, J. Závada, Tetrahedron 1992, 48, 9503; c) M. Hovorka, J. Závada, Tetrahedron 1992, 48, 9517.] It should be emphasized here that only specific naphtholcarboxylic acids are suitable as substrates.

To date, the unsymmetric biphenols have been prepared in a multistage synthesis sequence which comprised the protection of the phenolic hydroxyl group, the introduction of leaving groups and transition metal-catalyzed cross-coupling, and finally deprotection. [A review of C,C cross-couplings: C. Bolm, Org. Lett. 2012, 14, 2925.]

Modern methods enable direct electrochemical phenol-phenol and phenol-arene cross-coupling by use of BDD (=boron-doped diamond) [a.); A. Kirste, G. Schnakenburg, F. Stecker, A. Fischer, S. R. Waldvogel, Angew. Chem. Int. Ed. 2010, 49, 971-975; b) A. Kirste, B. Eisler, G. Schnakenburg, S. R. Waldvogel, J. Am. Chem. Soc. 2012, 134, 3571-3576, c) B. Eisler, D. Schollmeyer, K. M. Dyballa, R. Franke, S. R. Waldvogel, Angew. Chem. Int. Ed. 2014, 53, 5210-5213].

Scheme 2: Phenol-phenol cross coupling by means of selenium dioxide is presented in comparison with a conventional Suzuki coupling. Suzuki coupling is represented here in the two upper reaction equations. In the uppermost reaction, the hydroxyl function is protected and the boron substituent is introduced. In the second reaction step, the second phenol in which the hydroxyl group is likewise protected is cross-coupled by means of the palladium catalyst. The protecting group finally have to be removed again. By contrast, coupling by means of selenium dioxide is effected in one stage.

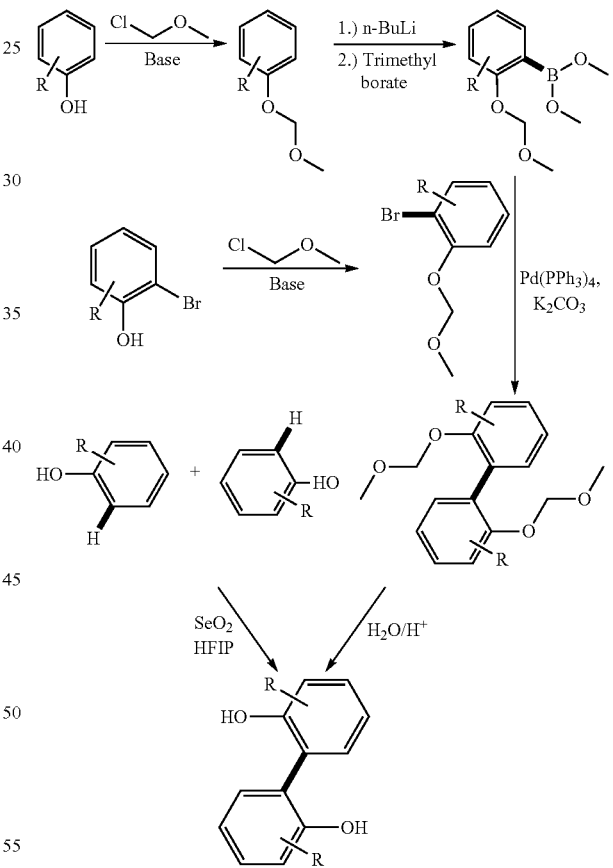

A great disadvantage of the abovementioned methods for phenol coupling is the need to operate in anhydrous solvents with exclusion of air. Superstoichiometric amounts of the relevant oxidizing agent are frequently required. The scarcity of raw materials (e.g. boron and bromine) leads to rising prices which leads to uneconomical processes. Multi-stage syntheses require the use of different solvents and multiple purification up to attainment of the desired product.

Preparation by electrochemical methods requires the use of sometimes costly conductive salts, the reusability of which cannot be ensured. The technical complexity of electrochemical reactions is also immense. Therefore, the preparation of large electrode surfaces of BDD is only possible to a limited extent and is linked with high costs. Even small defects in BDD surfaces moreover can lead to a complete destruction of the electrodes.

It was an object of the invention to provide a process which does not have the disadvantages described in connection with the prior art. More particularly, a process was to be provided in which two differently substituted phenols can be coupled to one another without any need for electrochemical processes and without having to work with bromine- or boron-containing leaving functionalities on the OH groups.

The object is achieved by a process as claimed in claim 1.

A process for preparing unsymmetric biphenols, comprising the process steps of:
a) adding a first substituted phenol to the reaction mixture,
b) adding a second substituted phenol having different substitution than the first phenol to the reaction mixture,
c) adding selenium dioxide to the reaction mixture,
d) adding a solvent,
e) heating the reaction mixture such that the first substituted phenol and the second phenol having different substitution are converted to an unsymmetric biphenol.

The sequence in which the two differently substituted phenols and the selenium dioxide are added to the reaction mixture is unimportant. In principle, further components may also be present in the reaction mixture, for example solvent, acid or base.

Advantageously, the present invention causes selective cross-coupling of two differently substituted phenols. According to the invention, this is accomplished through use of stoichiometric amounts of selenium dioxide, such that excess amounts of reagent waste are likewise advantageously avoided. Furthermore, the solvents used in accordance with the invention, especially 1,1,1,3,3,3-hexafluoroisopropanol (HFIP), can be recycled without significant losses. The compound HFIP is slightly acidic in water, since the electron-withdrawing $CF_3$ groups increase the acidity of the OH group. It is possible to recover the unconverted reactants by distillation.

The process according to the invention is advantageously less costly and time-consuming, since, in contrast to what has been described in the prior art, it is not necessary to protect any hydroxyl functions or insert leaving groups or use transition metal catalysts. In addition, there are no high capital costs, as would be necessary for the use of electrochemical methods. The process of the invention can be implemented inexpensively by known conventional industrial techniques.

In addition, according to the present invention, it is advantageously possible to work without exclusion of moisture in the reactants, and so no special apparatus setups that would have had to remove the water in the reactants are needed. This method enables simple and inexpensive conduct of C—C cross-couplings, and constitutes a method of interest by comparison with multistage syntheses.

Unconverted reactants and solvents used can be recovered by distillation and used for further reactions. Thus, the process according to the invention fulfills the requirements for an economic industrial scale process.

Moreover, selenium dioxide is used in the process according to the invention. Selenium dioxide is a waste product from metal purification and ore refining. Thus, in the process claimed here, a waste product from other processes is reused with addition of value. This is an important topic especially against the background of the sustainability of processes.

A further subject has been the synthesis of novel unsymmetric biphenols.

Preferably, the first phenol is a compound of the general formula (I):

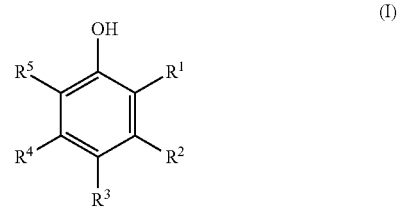

where $R^1$, $R^2$, $R^3$, $R^4$, $R^5$ are each independently selected from:
—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen,
two adjacent radicals may additionally be joined to one another to form a condensed system, and at least one of the $R^1$, $R^5$, $R^2$, $R^4$ radicals is —H,
where the alkyl and aryl groups mentioned may be substituted,
and the second phenol is a compound of the general formula (II):

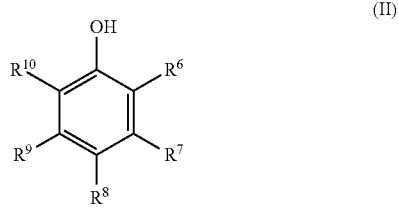

where $R^6$, $R^7$, $R^8$, $R^9$, $R^{10}$ are each independently selected from:
—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen,
two adjacent radicals may additionally be joined to one another to form a condensed system,
and at least one of the $R^6$, $R^{10}$, $R^7$, $R^9$ radicals is —H,
where the alkyl and aryl groups mentioned may be substituted,
and formula (I) is not the same as formula (II).

In the context of the present invention, the wording "formula (I) is not the same as formula (II)" is understood to mean that the substituents of the two phenols are different, such that, more particularly, no mirror plane can be placed onto the 2,2'-biphenol.

In a further variant, other unsymmetric biphenols prepared are 2,3'-biphenols which are already unsymmetric per se and on which it is likewise not possible to place a mirror plane.

In the context of the present invention, halogen is understood to mean fluorine, chlorine, bromine or iodine, especially chlorine and bromine.

($C_1$-$C_{12}$)-Alkyl and O—($C_1$-$C_{12}$)-alkyl may each be unsubstituted or substituted by one or more identical or different radicals selected from ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

$-(C_6-C_{20})$-Aryl and $-(C_6-C_{20})$-aryl-$(C_6-C_{20})$-aryl- may each be unsubstituted or substituted by one or more identical or different radicals selected from —H, $-(C_1-C_{12})$-alkyl, —O—$(C_1-C_{12})$-alkyl, —O—$(C_6-C_{20})$-aryl, $-(C_6-C_{20})$-aryl, -halogen, —COO—$(C_1-C_{12})$-alkyl, —CONH—$(C_1-C_{12})$-alkyl, $-(C_6-C_{20})$-aryl-CON$[(C_1-C_{12})$-alkyl$]_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N$[(C_1-C_{12})$-alkyl$]_2$.

In the context of the invention, the expression "—$(C_1-C_{12})$-alkyl" encompasses straight-chain and branched alkyl groups. Preferably, these groups are unsubstituted straight-chain or branched —$(C_1-C_8)$-alkyl groups and most preferably —$(C_1-C_6)$-alkyl groups. Examples of —$(C_1-C_{12})$-alkyl groups are especially methyl, ethyl, propyl, isopropyl, n-butyl, isobutyl, sec-butyl, tert-butyl, n-pentyl, 2-pentyl, 2-methylbutyl-, 3-methylbutyl-, 1,2-dimethylpropyl-, 1,1-dimethylpropyl, 2,2-dimethylpropyl-, 1-ethylpropyl-, n-hexyl-, 2-hexyl-, 2-methylpentyl-, 3-methylpentyl-, 4-methylpentyl-, 1,1-dimethylbutyl-, 1,2-dimethylbutyl-, 2,2-dimethylbutyl-, 1,3-dimethylbutyl-, 2,3-dimethylbutyl-, 3,3-dimethylbutyl-, 1,1,2-trimethylpropyl-, 1,2,2-trimethylpropyl-, 1-ethylbutyl-, 1-ethyl-2-methylpropyl-, n-heptyl-, 2-heptyl-, 3-heptyl-, 2-ethylpentyl-, 1-propylbutyl-, n-octyl-, 2-ethylhexyl-, 2-propylheptyl-, nonyl-, decyl- and dodecyl-.

In the context of the present invention, the expression "aryl" is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthranyl.

The elucidations relating to the expression "—$(C_1-C_{12})$-alkyl" also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

The expression "—$(C_3-C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl, tricyclyl or adamantyl. One example of a substituted cycloalkyl would be menthyl.

The expression "—$(C_3-C_{12})$-heterocycloalkyl groups", in the context of the present invention, encompasses nonaromatic, saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3-C_{12})$heterocycloalkyl groups are tetrahydrothiophenyl, tetrahydrofuryl, tetrahydropyranyl and dioxanyl.

In the context of the present invention, the expression "—$(C_6-C_{20})$-aryl and —$(C_6-C_{20})$-aryl-$(C_6-C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6-C_{10})$-aryl and —$(C_6-C_{10})$-aryl-$(C_6-C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6-C_{20})$-aryl groups and —$(C_6-C_{20})$-aryl-$(C_6-C_{20})$-aryl groups may have one or more (e.g. 1, 2, 3, 4 or 5) substituents, depending on the ring size. These substituents are preferably independently selected from —H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON$[(C_1-C_{12})$-alkyl$]_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N$[(C_1-C_{12})$-alkyl$]_2$.

Substituted —$(C_6-C_{20})$-aryl groups and —$(C_6-C_{20})$-aryl-$(C_6-C_{20})$-aryl groups are preferably substituted —$(C_6-C_{10})$-aryl groups and —$(C_6-C_{10})$-aryl-$(C_6-C_{10})$-aryl groups, especially substituted phenyl or substituted naphthyl or substituted anthracenyl. Substituted —$(C_6-C_{20})$-aryl groups preferably bear one or more, for example 1, 2, 3, 4 or 5, substituents selected from —$(C_1-C_{12})$-alkyl groups, —$(C_1-C_{12})$-alkoxy groups.

In one variant of the process, $R^1$, $R^2$, $R^3$, $R^4$, $R^5$, $R^6$, $R^7$, $R^8$, $R^9$, $R^{10}$ are each independently selected from:

—H, —$(C_1-C_{12})$-alkyl, —O—$(C_1-C_{12})$-alkyl, —$(C_6-C_{20})$-aryl, —O—$(C_6-C_{20})$-aryl, —Cl, —I, and at least one of the $R^1$, $R^5$, $R^2$ and $R^3$ radicals is —H, and at least one of the $R^6$, $R^{10}$, $R^7$ and $R^9$ radicals is —H, where the alkyl and aryl groups mentioned may be substituted, and formula (I) is not the same as formula (II).

In one variant of the process, $R^1$, $R^2$, $R^3$, $R^4$, $R^5$, $R^6$, $R^7$, $R^8$, $R^9$, $R^{10}$ are each independently selected from:

—H, —$(C_1-C_{12})$-alkyl, —O—$(C_1-C_{12})$-alkyl, —Cl, and at least one of the $R^1$, $R^5$, $R^2$ and $R^3$ radicals is —H, and at least one of the $R^6$, $R^{10}$, $R^7$ and $R^9$ radicals is —H, where the alkyl and aryl groups mentioned may be substituted, and formula (I) is not the same as formula (II).

In one variant of the process, $R^1$, $R^2$, $R^3$, $R^4$, $R^5$, $R^6$, $R^7$, $R^8$, $R^9$, $R^{10}$ are each independently selected from:

—H, —$(C_1-C_{12})$-alkyl, —O—$(C_1-C_{12})$-alkyl, and at least one of the $R^1$, $R^5$, $R^2$ and $R^3$ radicals is —H, and at least one of the $R^6$, $R^{10}$, $R^7$ and $R^9$ radicals is —H, where the alkyl and aryl groups mentioned may be substituted, and formula (I) is not the same as formula (II).

In one variant of the process, $R^1$ and $R^7$ are each H.
In one variant of the process, $R^1$ and $R^9$ are each H.
In one variant of the process, $R^1$ and $R^{10}$ are each H.
In one variant of the process, $R^5$ and $R^6$ are each H.
In one variant of the process, $R^1$ and $R^6$ are each H.
In one variant of the process, $R^5$ and $R^7$ are each H.
In one variant of the process, $R^5$ and $R^9$ are each H.
In one variant of the process, $R^5$ and $R^{10}$ are each H.
In one variant of the process, $R^{10}$ and $R^2$ are each H.
In one variant of the process, $R^{10}$ and $R^4$ are each H.
In one variant of the process, $R^6$ and $R^4$ are each H.
In one variant of the process, $R^6$ and $R^2$ are each H.
In one variant of the process, 2,3'-biphenols are formed.
In a further variant of the process, unsymmetric 2,2'-biphenols are formed.

In addition to the two differently substituted phenols and the selenium dioxide, the reaction mixture can also include a solvent, for example tetrahydrofuran, ethylene glycol dimethyl ether, bis(2-methoxyethyl) ether, diethyl ether, toluene, halogenated solvents or halogenated or non-halogenated acids. The purpose of the solvent is to ensure dissolution, mixing and stirrability of the different components with one another.

In one variant of the process of the invention, the halogenated solvent added is preferably a fluorinated carboxylic acid.

In one variant of the process of the invention, the solvent added is a fluorinated or chlorinated solvent.

In one variant of the process of the invention, the solvent added is a fluorinated solvent.

In one variant of the process, the solvent added is a fluorinated carboxylic acid or a fluorinated alcohol.

In one variant of the process of the invention, a carboxylic acid from the group of formic acid, acetic acid, propionic acid, trifluoroacetic acid is added.

In one variant of the process, formic acid is added.

In one variant of the process, the solvent added is trifluoroacetic acid or 1,1,1,3,3,3-hexafluoro-2-propanol (HFIP).

In one variant of the process, the solvent added is 1,1,1,3,3,3-hexafluoro-2-propanol (HFIP).

A particular advantage of the reaction systems described here is that they are not susceptible to moist ambient air, i.e. a mixture of water vapor, oxygen and nitrogen. Advantageously, it is therefore possible to avoid working under exclusion of air, which considerably simplifies the conduct of the reaction and actually enables it for industrial and economic purposes. The option of conducting the process in the presence of moist air is therefore of particular interest.

In one variant of the process, the selenium dioxide is added in a molar ratio based on the sum total of the first and second phenols within a range from 0.1 to 2.0. Preference is given here to the range from 0.25 to 1.5, and particular preference to the range from 0.4 to 1.2.

The fact that the selenium dioxide can be used in a substoichiometric amount is a further advantage over the reaction described in the prior art with other inorganic oxidizing agents, for example $AlCl_3$, $FeCl_3$ or $MnO_2$.

In one variant of the process, the reaction mixture is heated to a temperature in the range from 25° C. to 120° C. Preference is given here to the range from 30° C. to 100° C., and particular preference to the range from 30° C. to 60° C.

The temperatures specified here are the temperatures measured in the oil bath.

In one variant of the process, the heating is effected over a period in the range from 5 minutes to 24 hours. Preference is given here to the range from 15 minutes to 12 hours, and particular preference to the range from 15 minutes to 2.0 hours.

In one variant of the process, a 2,3'-biphenol is formed.

In one variant of the process, an unsymmetric 2,2'-biphenol is formed.

In one variant of the process, the process is conducted in the presence of moist air.

As well as the process, a novel biphenol is also claimed. This comprises, in accordance with the invention, 2,3'-biphenols and unsymmetric 2,2'-biphenols.

As well as the process, also claimed are inventive unsymmetric biphenols of the formulae 1, 2 or 6:

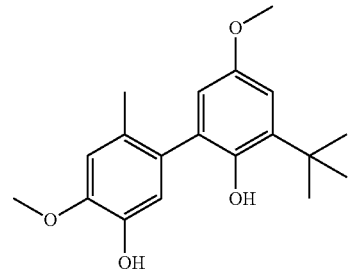

(1)

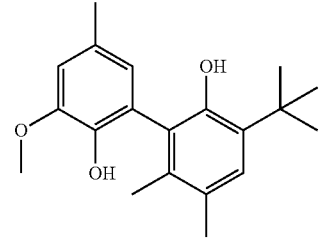

(2)

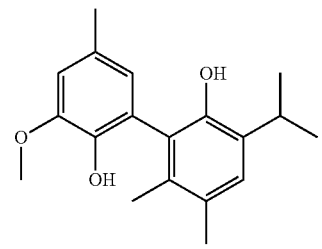

(6)

The invention is illustrated in detail hereinafter by working examples.

Analysis

Chromatography

The preparative liquid chromatography separations via flash chromatography were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-layer chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent: 5.6 g of molybdatophosphoric acid, 2.2 g of cerium(IV) sulfate tetrahydrate and 13.3 g of concentrated sulfuric acid to 200 mL of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from *Agilent Technologies, USA* (length: 30 m; internal diameter: 0.25 mm; film thickness of the covalently bound stationary phase: 0.25 µm; carrier gas: hydrogen; injector temperature: 250° C.; detector temperature: 310° C.; program: "hard" method: start temperature 50° C. for 1 min, heating rate: 15° C./min, end temperature 290° C. for 8 min). Gas chromatography-mass spectra (GCMS) of product mixtures and pure substances were recorded with the aid of the GC-2010 gas chromatograph combined with the GCMS-QP2010 mass detector from Shimadzu, Japan. Analysis is effected on an HP-1 quartz capillary column from *Agilent Technologies, USA* (length: 30 m; internal diameter: 0.25 mm; film thickness of the covalently bound stationary phase: 0.25 μm; carrier gas: hydrogen; injector temperature: 250° C.; detector temperature: 310° C.; program: "hard" method: start temperature 50° C. for 1 min, heating rate: 15° C./min, end temperature 290° C. for 8 min; GC-MS: ion source temperature: 200° C.).

Mass Spectrometry

All electrospray ionization analyses (ESI+) were conducted on a QTof Ultima 3 from Waters Micromasses, Milford, Mass. El mass spectra and the high-resolution El spectra were analyzed on an instrument of the MAT 95 XL sector field instrument type from Thermo Finnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The $^1$H and $^{13}$C spectra were calibrated according to the residual content of undeuterated solvent using the NMR Solvent Data Chart from Cambridge Isotopes Laboratories, USA. Some of the $^1$H and $^{13}$C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which need not correspond to IUPAC nomenclature.

General Procedures

GP1: Procedure for Cross-Coupling by Means of Selenium Dioxide

One equivalent of phenol component A was dissolved with one equivalent of phenol/arene component B in 4-6 mL of 1,1,1,3,3,3-hexafluoroisopropanol (HFIP) and the mixture treated with 0.5 equivalents of selenium dioxide. The mixture was heated to boiling with stirring. After a reaction time of 60-75 minutes, the reaction solution was filtered, diluted with ethyl acetate and washed with water. The organic phase was separated, dried over magnesium sulfate and the solvent removed by distillation under reduced pressure. The crude product thus obtained was purified by column chromatography on silica gel 60.

EXAMPLE 1

3-(tert-Butyl)-4',5-dimethoxy-6'-methyl-[1,1'-biphenyl]-2,3'-diol

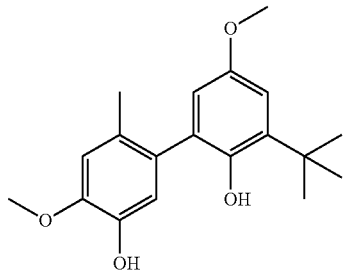

(1)

The reaction was conducted according to GP1 with 300 mg (2.17 mmol, 1.0 eq.) of 4-methylguaiacol and 387 mg (2.17 mmol, 1.0 eq.) of 4-methoxy-2-tert-butylphenol in 6 mL of HFIP and with addition of 120 mg (1.09 mmol, 0.5 eq.) of selenium dioxide. The reaction time was one hour. After extraction and removal of the solvent, the product mixture obtained was purified by means of column chromatography on silica gel 60 using 5:1 (cy:EA) as eluent. The product was obtained as a yellow highly viscous oil.

Yield: 103 mg (0.33 mmol, 24%)

$^1$H NMR (400 MHz, CDCl$_3$): δ [ppm]=1.36 (s, 3H), 1.69 (s, 3H), 3.73 (s, 3H), 3.81 (s, 3H), 6.16 (s, 1H), 6.32 (s, 1H), 6.81 (d, 1H, J=2.7 Hz), 6.95 (s, 1H, J=2.7 Hz)

$^{13}$C NMR (101 MHz, CDCl$_3$): δ [ppm]=29.16, 33.48, 34.50, 55.56, 55.99, 87.01, 102.46, 112.43, 114.14, 119.88, 123.15, 137.25, 151.72, 157.37, 168.23, 180.52

HRMS (ESI, pos.mode): m/z for $C_{19}H_{24}O_4[M+Na^+]$: calculated: 337.1416; found: 337.1416.

EXAMPLE 2

3'-tert-Butyl-2,2'-dihydroxy-3-methoxy-5,5',6'-trimethylbiphenyl

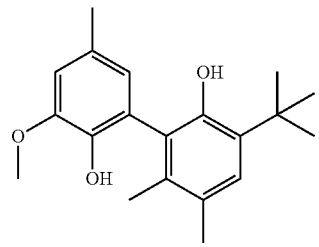

(2)

In a 50 mL round-bottom flask, 0.80 g of 2-tert-butyl-4,5-dimethylphenol (4.4 mmol) was dissolved together with 3.10 g of 4-methylguaiacol (22.4 mmol) in 35 mL of hexafluoroisopropanol and the mixture heated in a warm oil bath at 55° C. After 10 minutes, 0.49 g of selenium dioxide (4.4 mmol) was added. After 175 minutes, the reaction was terminated by addition of 8 mL of water and the hexafluoroisopropanol was distilled off under reduced pressure. The residue was taken up in 50 mL of ethyl acetate and washed twice with saturated sodium chloride solution. The organic phase was separated, dried over magnesium sulfate and the solvent distilled under reduced pressure. Excess 4-methylguaiacol was removed in a Kugelrohr oven (80° C., 1*10⁻³ mbar). The crude product purified by column chromatography. In this case, an automated column system from BÜCHI-Labortechnik GmbH, Essen was used. The column length was 32 cm and the diameter 6 cm. The eluent used was cyclohexane/ethyl acetate, operating with an ethyl acetate gradient of: 0% (over 5 min), 1-5% (over 5 min), 5% (over 10 min), 5-60% (10 min). The pumping rate was 100 mL/min.

Yield: 934 mg (2.9 mmol), 66%

GC: $t_R$(hard, HP-5)=14.629 min $^1$H NMR (400 MHz, CDCl$_3$) δ [ppm]=1.42 (s, 9H), 1.95 (s, 3H), 2.26 (s, 3H), 2.34 (s, 3H), 3.93 (s, 3H), 4.90 (s, 1H), 5.42 (s, 1H), 6.59-6.57 (m, 1H), 6.77 (d, J=1.7 Hz, 1H), 7.11 (s, 1H).

$^{13}$C NMR (100 MHz, CDCl$_3$) δ [ppm]=16.83, 20.20, 21.31, 29.81, 34.61, 56.09, 112.01, 121.40, 123.59, 123.94, 127.43, 128.18, 130.44, 132.93, 133.64, 141.63, 147.28, 149.76

HRMS (ESI, pos.mode): m/z for [M+Na$^+$]: calculated: 337.1780; found: 337.1783.

EXAMPLE 3

3',5'-Di-tert-butyl-2,2'-dihydroxy-3-methoxy-5-methylbiphenyl

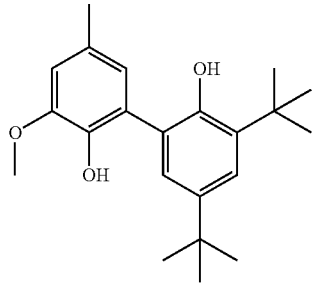

(3)

In a 50 mL round-bottom flask, 0.80 g of 2,4-di-tert-butylphenol (3.8 mmol) was dissolved together with 2.68 g of 4-methylguaiacol (19.4 mmol) in 32 mL of hexafluoroisopropanol and the mixture heated in a warm oil bath at 55° C. After 10 minutes, 0.43 g of selenium dioxide (3.8 mmol) was added. After 110 minutes, the reaction was terminated by addition of 8 mL of water and the hexafluoroisopropanol was distilled off under reduced pressure. The residue was taken up in 50 mL of ethyl acetate and washed twice with saturated sodium chloride solution. The organic phase was separated, dried over magnesium sulfate and the solvent distilled under reduced pressure. The crude product purified by column chromatography. In this case, an automated column system from BÜCHI-Labortechnik GmbH, Essen was used. The column length was 16 cm and the diameter 6 cm. The eluent used was cyclohexane/ethyl acetate, operating with an ethyl acetate gradient of: 0% (over 5 min), 1-5% (over 5 min), 5% (over 10 min), 5-60% (10 min). The pumping rate was 100 mL/min. In order to remove residues of 4-methylguaiacol from the product, the product was treated in a Kugelrohr oven (80° C., 1*10⁻³ mbar).

Yield: 0.306 g (0.9 mmol), 23%

GC: $t_R$(hard, HP-5)=14.751 min $^1$H NMR (400 MHz, CDCl$_3$) δ [ppm]=1.40 (s, 9H), 1.53 (s, 9H), 2.40 (s, 3H), 3.95 (s, 3H), 6.07 (s, 1H), 6.11 (s, 1H), 6.78 (d, J=1.6 Hz, 1H), 6.80-6.81 (m, 1H), 7.20 (d, J=2.5 Hz, 1H), 7.43 (d, J=2.5 Hz, 1H).

$^{13}$C NMR (100 MHz, CDCl$_3$) δ [ppm]=21.33, 30.00, 31.81, 34.50, 35.34, 56.24, 111.13, 124.03, 124.27, 124.64, 125.28, 125.62, 130.54, 136.85, 139.81, 142.46, 146.56, 149.95.

HRMS (ESI, pos.mode): m/z for [M+Na$^+$]: calculated: 365.2093; found: 365.2087.

EXAMPLE 4

3'-tert-Butyl-2,2'-dihydroxy-5,5'-dimethyl-3-methoxybiphenyl

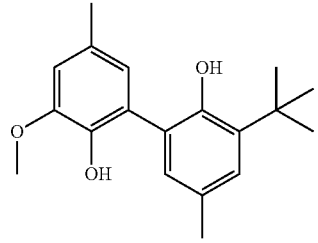

(4)

In a 50 mL round-bottom flask, 0.70 g of 2-tert-butyl-4-methylphenol (4.2 mmol) was dissolved together with 2.94 g of 4-methylguaiacol (21.3 mmol) in 35 mL of hexafluoroisopropanol and the mixture heated in a warm oil bath at 55° C. After 10 minutes, 0.47 g of selenium dioxide (4.2 mmol) was added. After 110 minutes, the reaction was terminated by addition of 8 mL of water and the hexafluoroisopropanol was distilled off under reduced pressure. The residue was taken up in 50 mL of ethyl acetate and washed twice with saturated sodium chloride solution. The organic phase was separated, dried over magnesium sulfate and the solvent distilled under reduced pressure. Excess 4-methylguaiacol was removed in a Kugelrohr oven (80° C., 1*10⁻³ mbar). The crude product purified by column chromatography. In this case, an automated column system from BÜCHI-Labortechnik GmbH, Essen was used. The column length was 32 cm and the diameter 6 cm. The eluent used was cyclohexane/ethyl acetate, operating with an ethyl acetate gradient of: 0% (over 5 min), 1-5% (over 5 min), 5% (over 10 min), 5-60% (10 min). The pumping rate was 100 mL/min.

Yield: 0.492 g (1.6 mmol), 39%

GC: $t_R$(hard, HP-5)=14.306 min $^1$H NMR (400 MHz, CDCl$_3$) δ [ppm]=1.46 (s, 9H), 2.33 (s, 3H), 2.35 (s, 3H), 3.93 (s, 3H), 6.00 (s, 1H), 6.02 (s, 1H), 6.74 (bs, 2H), 6.96 (d, J=1.6 Hz, 1H), 7.14 (d, J=1.6 Hz, 1H).

$^{13}$C NMR (100 MHz, CDCl$_3$) δ [ppm]=20.96, 21.23, 29.86, 34.96, 56.18, 111.07, 124.08, 124.13, 125.86, 127.57, 129.07, 129.13, 130.41, 137.48, 139.73, 146.45, 150.00

HRMS (ESI, pos.mode): m/z for [M+Na$^+$]: calculated: 323.1623; found: 323.1626.

EXAMPLE 5

2,2'-Dihydroxy-3-methoxy-3',5,5'-trimethylbiphenyl

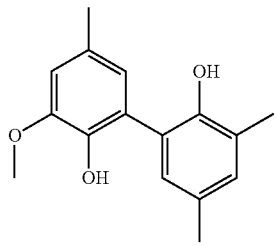

(5)

In a 100 mL round-bottom flask, 0.80 g of 2,4-dimethylphenol (6.5 mmol) was dissolved together with 4.52 g of 4-methylguaiacol (32.3 mmol) in 54 mL of hexafluoroisopropanol and the mixture heated in a warm oil bath at 55° C. After 10 minutes, 0.72 g of selenium dioxide (6.5 mmol) was added. After 120 minutes, the reaction was terminated by addition of 8 mL of water and the hexafluoroisopropanol was distilled off under reduced pressure. The residue was taken up in 50 mL of ethyl acetate and washed twice with saturated sodium chloride solution. The organic phase was separated, dried over magnesium sulfate and the solvent distilled under reduced pressure. Excess 4-methylguaiacol was removed in a Kugelrohr oven (80° C., 1*10⁻³ mbar). The crude product was purified by column chromatography. The column length was 26 cm with a diameter of 3 cm. The eluent used was a mixture of cyclohexane and ethyl acetate (9:1). The fraction size was 20 mL. After 60 fractions, the eluent was switched to an eluent mixture of cyclohexane/ethyl acetate in a ratio of 8:2.

Yield: 0.184 g (0.7 mmol), 10%
GC: $t_R$(hard, HP-5)=13.542 min
$^1$H NMR (400 MHz, CDCl$_3$) δ [ppm]=2.31 (s, 3H), 2.32 (s, 3H), 2.35 (s, 3H), 3.93 (s, 3H), 6.73-6.74 (m, 1H), 6.74.6.76 (m, 1H), 6.94-6.95 (m, 1H), 6.99-7.01 (m, 1H).
$^{13}$C NMR (100 MHz, CDCl$_3$) δ [ppm]=16.62, 20.65, 21.32, 56.26, 111.02, 124.06, 124.20, 124.70, 126.27, 128.91, 129.70, 130.51, 131.52, 139.57, 146.44, 149.52.
HRMS (ESI, pos.mode): m/z for [M+Na$^+$]: calculated: 281.1154; found: 281.1151.

EXAMPLE 6

2,2'-Dihydroxy-3'-isopropyl-3-methoxy-5,5',6'-trimethylbiphenyl

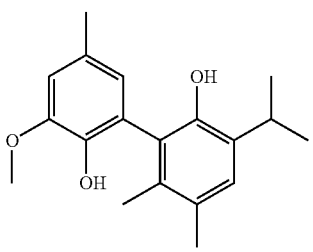

(6)

In a 50 mL round-bottom flask, 0.70 g of 4,5-dimethyl-2-isopropylphenol (4.2 mmol) were dissolved together with 2.94 g of 4-methylguaiacol (21.3 mmol) in 35 mL of hexafluoroisopropanol and the mixture heated in a warm oil bath at 55° C. After 10 minutes, 0.47 g of selenium dioxide (4.2 mmol) was added. After 175 minutes, the reaction was terminated by addition of 8 mL of water and the hexafluoroisopropanol was distilled off under reduced pressure. The residue was taken up in 50 mL of ethyl acetate and washed twice with saturated sodium chloride solution. The organic phase was separated, dried over magnesium sulfate and the solvent distilled under reduced pressure. Excess 4-methylguaiacol was removed in a Kugelrohr oven (80° C., 1*10⁻³ mbar). The crude product purified by column chromatography. In this case, an automated column system from BÜCHI-Labortechnik GmbH, Essen was used. The column length was 32 cm and the diameter 6 cm. The eluent used was cyclohexane/ethyl acetate, operating with an ethyl acetate gradient of: 0% (over 5 min), 1-5% (over 5 min), 5% (over 10 min), 5-60% (10 min). The pumping rate was 100 mL/min.

Yield: 564 mg (1.8 mmol), 44%
GC: $t_R$(hard, HP-5)=14.385 min
$^1$H NMR (400 MHz, CDCl$_3$) δ [ppm]=1.27 (s, J=6.9 Hz, 6H), 1.98 (s, 3H), 2.27 (s, 3H), 2.34 (s, 3H), 3.29 (hept, J=6.9 Hz, 1H), 4.77 (s, 1H), 5.47 (s, 1H), 6.59 (d, J=1.7 Hz, 1H), 6.77 (d, J=1.7 Hz, 1H), 7.04 (s, 1H).
$^{13}$C NMR (100 MHz, CDCl$_3$) δ [ppm]=16.85, 20.14, 21.28, 22.95, 27.17, 56.09, 111.89, 121.59, 123.03, 123.54, 127.48, 128.06, 130.32, 131.66, 133.13, 141.49, 147.21, 148.38.
HRMS (ESI, pos.mode): m/z for [M+Na$^+$]: calculated: 323.1623; found: 323.1625.

The results show that the process of the invention is a synthesis route with which cross-coupled biphenols can be prepared selectively and in good to very good yields. In addition, it has been possible in this way to prepare novel compounds.

What is claimed is:
1. A process for preparing unsymmetric biphenols, comprising the process steps of:
  a) adding a first substituted phenol to the reaction mixture,
  b) adding a second substituted phenol having different substitution than the first phenol to the reaction mixture,
  c) adding selenium dioxide to the reaction mixture,
  d) adding a solvent,
  e) heating the reaction mixture such that the first substituted phenol and the second phenol having different substitution are converted to an unsymmetric biphenol;
  wherein a 2,3'-biphenol is formed.
2. The process as claimed in claim 1, wherein the first phenol is a compound of the general formula (I):

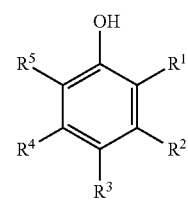

(I)

where R$^1$, R$^2$, R$^3$, R$^4$, R$^5$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen, two adjacent radicals may additionally be joined to one another to form a condensed system, and at least one of the $R^1$, $R^5$, $R^2$, $R^4$ radicals is —H, where the alkyl and aryl groups mentioned may be substituted, and the second phenol is a compound of the general formula (II):

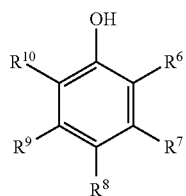

(II)

where $R^6$, $R^7$, $R^8$, $R^9$, $R^{10}$ are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, -halogen two adjacent radicals may additionally be joined to one another to form a condensed system, and at least one of the $R^6$, $R^{10}$, $R^7$, $R^9$ radicals is —H, where the alkyl and aryl groups mentioned may be substituted, and formula (I) is not the same as formula (II).

3. The process as claimed in claim 2, wherein the $R^1$, $R^2$, $R^3$, $R^4$, $R^5$ $R^6$, $R^7$, $R^8$, $R^9$, $R^{10}$ radicals are each independently selected from:

—H, —($C_1$-$C_{12}$)-alkyl, —O—($C_1$-$C_{12}$)-alkyl, —($C_6$-$C_{20}$)-aryl, —O—($C_6$-$C_{20}$)-aryl, —Cl, —I, and at least one of the $R^1$, $R^5$, $R^2$ and $R^3$ radicals is —H, and at least one of the $R^6$, $R^{10}$, $R^7$ and $R^9$ radicals is —H, where the alkyl and aryl groups mentioned may be substituted, and formula (I) is not the same as formula (II).

4. The process as claimed in claim 2, wherein the $R^1$, $R^2$, $R^3$, $R^4$, $R^5$ $R^6$, $R^7$, $R^8$, $R^9$, $R^{10}$ radicals are each independently selected from:

—H, —($C_1$-$C_{12}$)-alkyl, —O—($C_1$-$C_{12}$)-alkyl and at least one of the $R^1$, $R^5$, $R^2$ and $R^3$ radicals is —H, and at least one of the $R^6$, $R^{10}$, $R^7$ and $R^9$ radicals is —H, where the alkyl and aryl groups mentioned may be substituted, and formula (I) is not the same as formula (II).

5. The process as claimed in claim 1, wherein a halogenated solvent is added in process step d).

6. The process as claimed in claim 1, wherein the solvent added is a fluorinated or chlorinated solvent.

7. The process as claimed in claim 1, wherein the solvent added is a fluorinated solvent.

8. The process as claimed in claim 1, wherein the fluorinated solvent added is 1,1,1,3,3,3-hexafluoro-2-propanol or trifluoroacetic acid.

9. The process as claimed in claim 1, wherein the selenium dioxide is added in a molar ratio based on the sum total of the first and second phenols within a range from 0.1 to 2.0.

10. The process as claimed in claim 1, wherein the reaction mixture is heated to a temperature in the range from 25° C. to 120° C.

11. The process as claimed in claim 1, wherein the heating is effected over a period in the range from 5 minutes to 24 hours.

12. The process as claimed in claim 1, wherein the process is conducted in the presence of moist air.

* * * * *